United States Patent
Rhee

(10) Patent No.: US 6,585,671 B2
(45) Date of Patent: Jul. 1, 2003

(54) HYBRID-MESH CAST SLEEVE AND METHOD

(76) Inventor: Kun Young Rhee, #A-310 Samik Apt. 51 Yoido-dong, Young Dung Po-gu, Seoul PO 150-010 (KR)

( * ) Notice: Subject to any disclaimer, the term of this patent is extended or adjusted under 35 U.S.C. 154(b) by 0 days.

(21) Appl. No.: 09/952,620

(22) Filed: Sep. 11, 2001

(65) Prior Publication Data

US 2003/0093025 A1 May 15, 2003

(51) Int. Cl.⁷ ................................................. A61F 5/00
(52) U.S. Cl. ................................ 602/5; 602/8; 602/62
(58) Field of Search ..................... 602/5, 6, 7, 8, 602/20, 23; 128/846, 869, 878, 879

(56) References Cited

U.S. PATENT DOCUMENTS

| | | | | |
|---|---|---|---|---|
| 4,668,563 A | * | 5/1987 | Buese | 428/230 |
| 5,273,802 A | * | 12/1993 | Scholz | 602/8 |
| 5,931,798 A | * | 8/1999 | Green | 602/6 |
| 6,159,877 A | * | 12/2000 | Scholz | 602/8 |

* cited by examiner

*Primary Examiner*—Michael A. Brown
(74) *Attorney, Agent, or Firm*—Burns Doane Swecker & Mathis, LLP

(57) ABSTRACT

The hybrid-mesh cast sleeve invention comprises a tubular mesh woven of an elastic yarn and a coarse, impregnable yarn. In use, a stockinette, then a hybrid-mesh cast sleeve impregnated with a hardening agent, are positioned around a part of the body of a human or other animal to be reinforced by a cast. Solidification of the hardening agent produces a solid cast with a plurality of air vents.

5 Claims, 2 Drawing Sheets

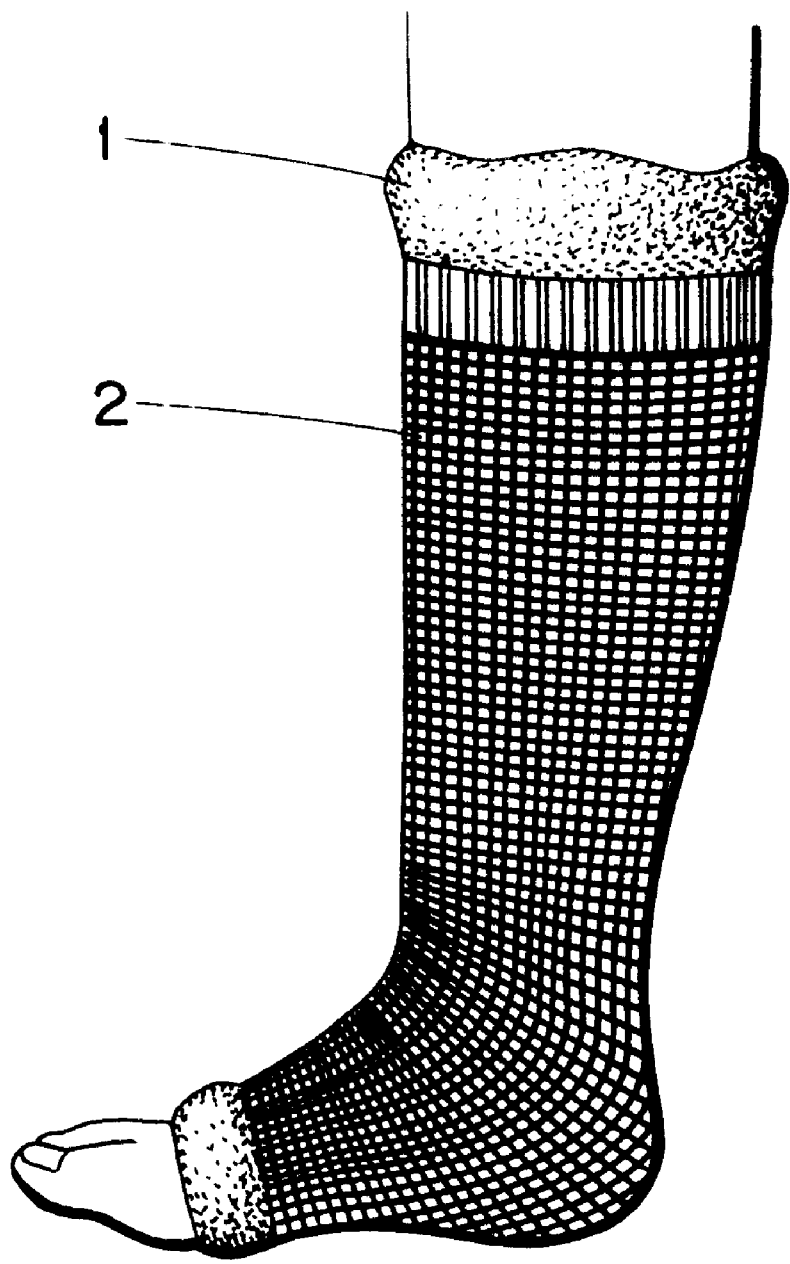

HYBRID-MESH CAST SLEEVE AND METHOD

BACKGROUND OF THE INVENTION

1. Field of the Invention

The present invention relates to casts used for orthopedics and other fields of medicine. More particularly, the present invention relates to a woven material used to build a cast around a part of the body of a human or other animal.

2. Description of the Related Art

Traditional casts typically depend upon skilled personnel, such as physicians, manually building a cast to protect and align a part of the body of a human or other animal containing a fractured bone, thereby facilitating proper fusion of the fractured bone. A common method for building casts involves applying a sheep skin cloth, stockinette, or equivalent (collectively, "stockinette") in the area around the fractured bone ("desired area"), and iterations of impregnating swaths of cloth, usually cotton, with a hardening agent, such as hardening latex or a synthetic resin (collectively, "hardening agent"), and of layering the swaths of cloth, before the swaths harden, around the stockinette. The hardening of the hardening agent (originally Plaster of Paris, but today synthetic resins are more commonly used) permeating the layered swaths transforms the layered swaths into a cast. After each application of cloth swathing hardens, another layer is applied in similar fashion until the desired cast stiffness is obtained.

The traditional method of building a cast has several problems: First, personnel skilled in cast-making are required, especially in creating the edges of a cast, spacing the spirals of swathing, judging the number of layers necessary for protection of the bone fusion process, and abrading the surface of each successive layer to eliminate gaps between layers. This is a time-consuming, difficult process. Second, traditional casts do not "breathe" very well, i.e., the hardened cast does not allow the free exchange of air between the skin surface under the cast and the atmosphere. Poor cast breathing can lead to itchy or even infected skin conditions. Third, casts with irregular surfaces can cause blistering, and worse, improper fusion of bones. Fourth, traditional casts are radio-opaque, that is, X-rays cannot penetrate a traditional cast, which prevents X-ray imaging through the cast. The inability to use X-ray imaging deprives the treating physician of information about healing of bone fractures. Fifth, traditional casts can not be subjected to prolonged contact with water, so bathing or showering by the cast-wearer becomes problematic.

U.S. Pat. No. 3,826,252, granted to Laico, and U.S. Pat. No. 4,381,769, granted to Prahl, disclose methods and apparatus for creating improved cast edges. U.S. Pat. No. 5,725,487, granted to Freeman, et al., discloses an orthopedic casting tape, and U.S. Pat. No. 5,522,241 discloses an orthopedic casting band. The related art represented by these patents are incremental improvements in the art of casting, but all required skilled personnel to avoid the problems of a weak cast, poor edges and breathing, and irregular surfaces. There has long been a need for a simpler method of cast building, especially one that did not require highly skilled personnel, created comfortable cast edges, permitted breathing, and minimized irregularities in cast construction.

SUMMARY OF THE INVENTION

The hybrid-mesh cast sleeve invention comprises a tubular mesh, or "sleeve", woven of an elastic yarn and an impregnable yarn. The hybrid-mesh cast sleeve is used with a hardening agent to produce a cast for orthopedics and other fields of medicine. Although the term "sleeve" is used, the hybrid-mesh cast sleeve invention can be made in various diameters for use on parts of the body other than an arm or leg. The hybrid-mesh cast sleeve can also be broadly used on animals, especially domesticated animals. A cast using the hybrid-mesh cast sleeve can be built by personnel without specialized training in using traditional "wrapping" methods of cast construction, and the cast created is a breathable cast with comfortable cast edges and minimal cast irregularities.

BRIEF DESCRIPTION OF THE DRAWINGS

The above objects, features and advantages of the present invention will become more apparent from the following detailed description when taken in conjunction with the accompanying drawings, in which.

DETAILED DESCRIPTION OF THE PREFERRED EMBODIMENT

Figure 1:
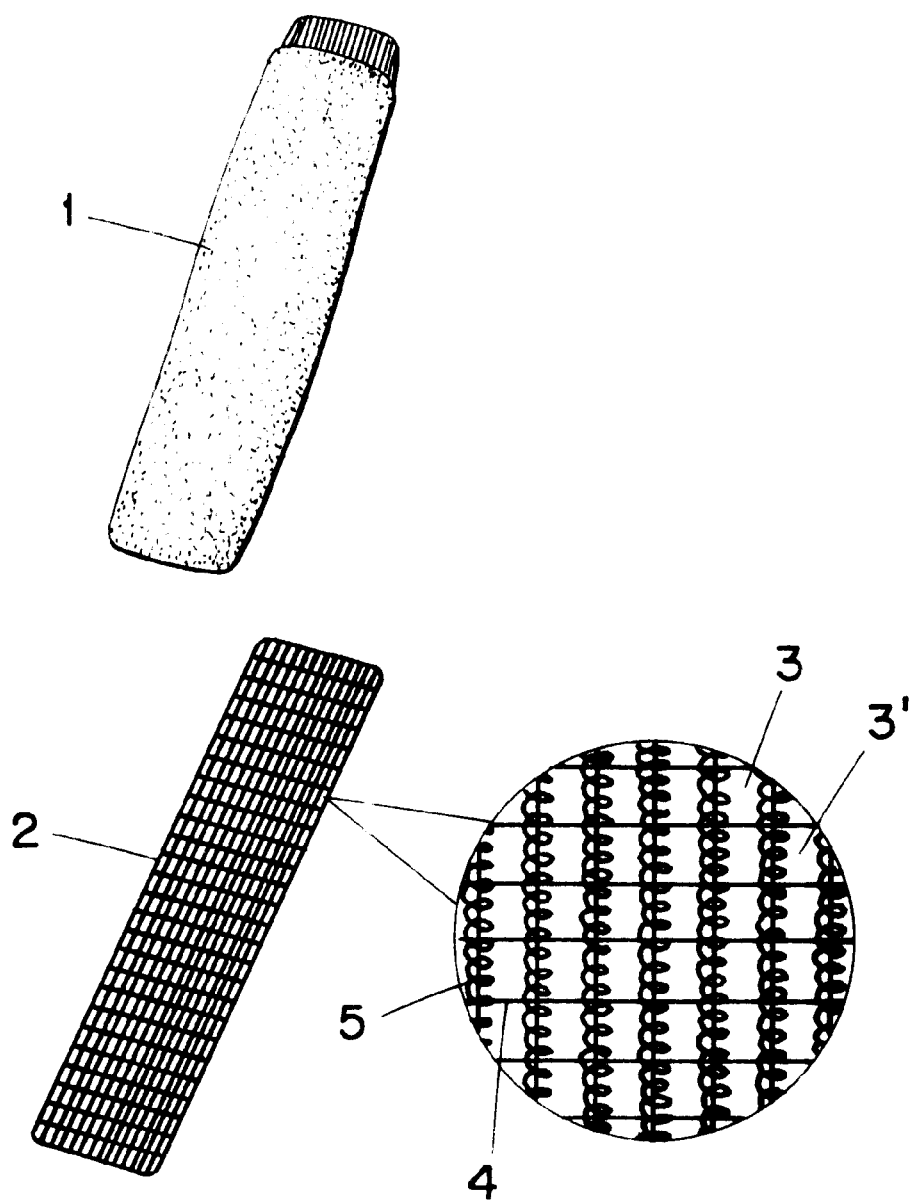
FIG. 1 illustrates a top view of the fabric of the hybrid-mesh cast sleeve; and, FIG. 2 illustrates a side view showing a completed cast using a hybrid-mesh cast sleeve.

A preferred embodiment of the present invention will now be described with reference to the accompanying drawings. In the following description, the same drawing reference numerals are used for the same elements in different Figures.

As shown in FIG. 1 the hybrid-mesh cast sleeve (2) is a tubular mesh woven using a coarse, impregnable yarn (4) and an elastic stretch yarn (5). The tightness of the weave of the tubular mesh and the diameter of the yarns are selected so that air vents (3, 3') remain after hardening of a hardening agent introduced into the tubular mesh. The hybrid-mesh cast sleeve is preferably used with a stockinette (1), as explained below.

As shown in FIG. 2, to use the hybrid-mesh cast sleeve, a stockinette of suitable diameter, length, and thickness is pulled on around the area of a body to be reinforced by a cast so that the stockinette is worn by the patient or animal being treated in a band-like or annular manner around the desired area. The preferred stockinette is made of polypropylene (CAS No. 9003-07-0). The length of the stockinette is selected so that the ends of the stockinette will protrude from each end of the hybrid-mesh cast sleeve when the hybrid-mesh cast sleeve is placed around the desired area. A single stockinette has traditionally been used in cast construction, and a single layer stockinette can be used with the hybrid-mesh cast sleeve. However, better results can be obtain by using two stockinettes, a very thin stockinette applied next to the skin in the desired area, and a thicker stockinette applied over the very thin stockinette. Using two stockinettes improves breathability. Before application of the hybrid-mesh cast sleeve, the sleeve is soaked in a hardening agent, usually a synthetic resin or a hardening latex. Before the hardening agent impregnating the hybrid-mesh cast sleeve begins to solidify, the hybrid-mesh cast sleeve is positioned so that the impregnated hybrid-mesh cast sleeve covers the midsection of the stockinette and the area to be reinforced by a cast (typically the area of a bone fracture), and the ends of the stockinette protrude beyond the edges of the cast sleeve. Many of the gaps (3, 3', in FIG. 1) between the coarse yarn (4, in FIG. 1) and the elastic yarn (5, in FIG. 1) remain open after the hardening agent has solidified, thereby creating a plurality of vents and a breathable cast.

While a conventional "wrapped" cast comprises 4 to 6 layers of cloth swathing, the hybrid-mesh cast invention comprises only one layer, and is therefore easier to store, retrieve, and apply. Unlike the construction of a conventional "wrapped" cast, when a hybrid-mesh cast sleeve is used, it is not necessary to abrade the surface of each successive layer to eliminate gaps between layers. The hybrid-mesh cast sleeve can be installed quickly and easily. The similarity between pulling on a sweater or a pair of socks and positioning a hybrid-mesh cast sleeve around a desired area means that a hybrid-mesh cast can be properly installed by a medical or veterinary technician, a military medic, or someone of similar skill level, and does not require the skills of physicians, veterinarians, or nurses.

In short, the use of a hybrid-mesh cast sleeve does not require specialized training in using traditional "wrapping" methods of cast construction, and the cast created is a breathable cast with comfortable cast edges and minimal cast irregularities. The hybrid-mesh cast sleeve can be installed quickly and easily, and does not have irregular surfaces that cause blistering, and worse, improper fusion of bones. After installation, the hybrid-mesh cast sleeve is not radio-opaque. X-ray imaging can be used successfully in the cast area and the resulting X-rays provide excellent clarity of bones, bone growth, and other features in the area enclosed by the cast. Finally, after installation, prolonged contact with water has no effect of the hybrid-mesh cast sleeve, so there is no limitation on bathing or showering by or of the cast-wearer.

While the invention has been shown and described with reference to certain preferred embodiments thereof, it will be understood by those skilled in the art that various changes in form and details may be made therein without departing from the spirit and scope of the invention as defined by the appended claims.

I claim:

1. A combination for constructing a cast, comprising:
   a stockinette for positioning around an area of body of a human or animal to be reinforced by a cast;
   a hybrid-mesh cast fabric impregnated with a hardening agent,
   wherein the impregnated hybrid-mesh cast fabric is to be positioned so that the hybrid-mesh cast fabric covers the mid-section of the stockinette and an area to be reinforced by a cast, to thereby produce a solid cast with a plurality of air vents upon the solidification of the hardening agent that impregnates the hybrid-cast fabric.

2. A fabric for use in making a cast, comprising a mesh woven including an elastic yarn and an impregnable yarn that is impregnated with a hardening agent before positioning the mesh on a body part, and in which the fabric tightness of the weave and diameter of the yarns are selected so that air vents remain after hardening of the hardening agent introduced into the tubular mesh, and wherein the mesh is tubular before application and initially flexible so that it can be put on to the body part without wrapping and then hardened.

3. A method for constructing a cast, comprising:
   positioning a stockinette around an area of the body of a human or other animal to be reinforced by a cast;
   impregnating a hybrid-mesh cast sleeve with a hardening agent; and
   positioning the impregnated hybrid-mesh cast sleeve so that the hybrid-mesh cast sleeve covers the midsection of the stockinette and the area to be reinforced by a cast, thereby producing a solid cast with a plurality of air vents upon the solidification of the hardening agent that impregnates the hybrid-mesh cast sleeve.

4. A cast constructed according to the method of claim 3.

5. A method for constructing a cast in accordance with claim 3, wherein the step of positioning a stockinette includes positioning a first and a second stockinette, wherein the first stockinette is a relatively thin stockinette applied around an area of the body of a human or other animal to be reinforced by a cast, and a thicker stockinette applied over the thin stockinette.

* * * * *